US010918393B2

(12) United States Patent
Brodaczewski et al.

(10) Patent No.: US 10,918,393 B2
(45) Date of Patent: Feb. 16, 2021

(54) SURGICAL APPLIANCE

(71) Applicant: Grena USA LLC, Wilmington, DE (US)

(72) Inventors: Wieslaw Mieczyslaw Brodaczewski, Dubai (AE); Andrzej Janusz Decewicz, Nottingham (GB); Grzegorz Andrzej Wawryniuk, Warsaw (PL)

(73) Assignee: GRENA USA LLC, Wilmington, DE (US)

( * ) Notice: Subject to any disclaimer, the term of this patent is extended or adjusted under 35 U.S.C. 154(b) by 197 days.

(21) Appl. No.: 16/169,681

(22) Filed: Oct. 24, 2018

(65) Prior Publication Data

US 2019/0133596 A1      May 9, 2019

Related U.S. Application Data

(60) Provisional application No. 62/581,729, filed on Nov. 5, 2017.

(51) Int. Cl.
*A61B 17/128* (2006.01)
*A61B 17/10* (2006.01)
(Continued)

(52) U.S. Cl.
CPC .......... *A61B 17/1285* (2013.01); *A61B 17/10* (2013.01); *A61B 17/282* (2013.01);
(Continued)

(58) Field of Classification Search
CPC ......... A61B 34/70; A61B 34/71; A61B 17/29; A61B 17/2909; A61B 2017/0046;
(Continued)

(56) References Cited

U.S. PATENT DOCUMENTS 2,790,437 A * 4/1957 Moore ................... A61B 10/06
600/564
5,330,502 A   7/1994 Hassler
(Continued)

FOREIGN PATENT DOCUMENTS

AU   2014218433 A1   9/2014
AU   2014277777 A1   1/2015
(Continued)

OTHER PUBLICATIONS

Karl Storz, Laproscopy in Surgery, Gynecology, Urology, Eighth Edition, p. 236.

*Primary Examiner* — Wade Miles
*Assistant Examiner* — Mohammed S Adam
(74) *Attorney, Agent, or Firm* — Seth Natter; Natter & Natter

(57) ABSTRACT

A surgical appliance includes an elongate barrel having effector jaws mounted to a carrier secured to the distal end of the barrel. A handle includes a grip for opening and closing the effector jaws, a knob for articulating the carrier, a knob for rotating the barrel and a safety mechanism for automatically preventing inadvertent actuation of the grip. Each jaw pivots about a pin and is actuated by a rod which is engaged by the grip. A lever is pivotally mounted to the handle and includes a latch which blocks movement of the grip unless the lever is pivoted in a proximal direction against a spring bias. When the lever is released, the latch automatically returns to the blocking position. A toggle arm fixed to a cam shaft can be rotated such that a cam moves the latch to the disengaged position for repeated grip actuation.

19 Claims, 10 Drawing Sheets

(51) Int. Cl.
   *A61B 17/29* (2006.01)
   *A61B 17/28* (2006.01)
   *A61B 17/122* (2006.01)
   *A61B 17/00* (2006.01)
   *A61B 18/00* (2006.01)

(52) U.S. Cl.
   CPC ........ *A61B 17/2909* (2013.01); *A61B 17/122* (2013.01); *A61B 17/2816* (2013.01); *A61B 17/2833* (2013.01); *A61B 2017/0046* (2013.01); *A61B 2017/00398* (2013.01); *A61B 2017/292* (2013.01); *A61B 2017/2913* (2013.01); *A61B 2017/2927* (2013.01); *A61B 2017/2929* (2013.01); *A61B 2017/2946* (2013.01); *A61B 2018/0063* (2013.01)

(58) Field of Classification Search
   CPC .... A61B 2017/2902; A61B 2017/2903; A61B 2017/2912; A61B 2017/2919; A61B 2017/292; A61B 2017/2925; A61B 2017/2932; A61B 2017/294; A61B 10/06; A61B 17/2841; A61B 2017/1125; A61B 2017/2845; A61B 2017/2913
   See application file for complete search history.

(56) References Cited

U.S. PATENT DOCUMENTS

| | | | |
|---|---|---|---|
| 5,425,743 A * | 6/1995 | Nicholas | ............ A61B 17/2909 606/151 |
| 5,746,740 A | 5/1998 | Nicholas | |
| 5,797,536 A | 8/1998 | Smith | |
| 6,019,780 A | 2/2000 | Lombardo | |
| 6,733,514 B2 | 5/2004 | Miser | |
| 7,431,188 B1 | 10/2008 | Marczyk | |
| 8,628,545 B2 | 1/2014 | Cabrera | |
| 8,961,542 B2 | 2/2015 | Whitfield | |
| 8,968,337 B2 | 3/2015 | Whitfield | |
| 9,271,723 B2 | 3/2016 | Taylor et al. | |
| 2009/0088792 A1 | 4/2009 | Hoell | |
| 2012/0016391 A1 | 1/2012 | Aguirre | |
| 2013/0296922 A1 | 11/2013 | Allen | |
| 2016/0066919 A1 | 3/2016 | Dannaher | |
| 2016/0151082 A1 | 6/2016 | Allen, IV et al. | |
| 2016/0361107 A1 | 12/2016 | Zergiebel et al. | |

FOREIGN PATENT DOCUMENTS

| | | |
|---|---|---|
| EP | 2823775 A2 | 1/2015 |
| WO | 2006071120 A1 | 7/2006 |

* cited by examiner

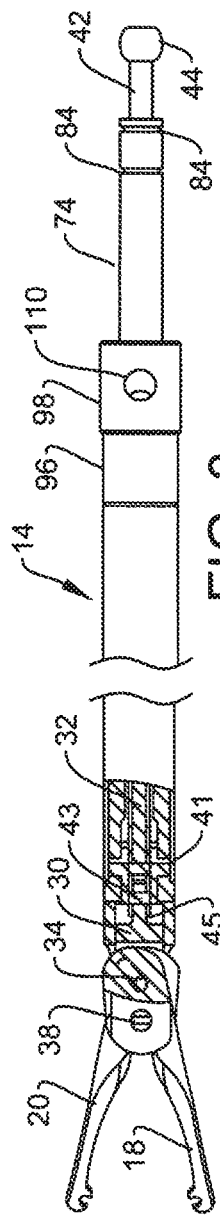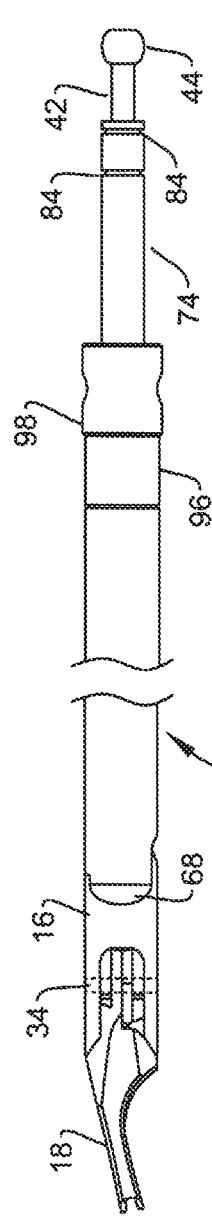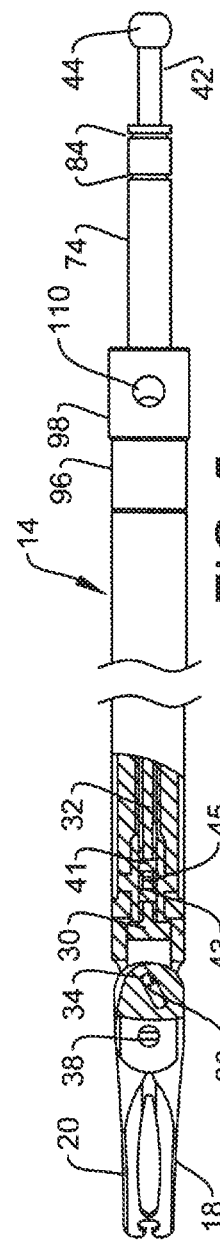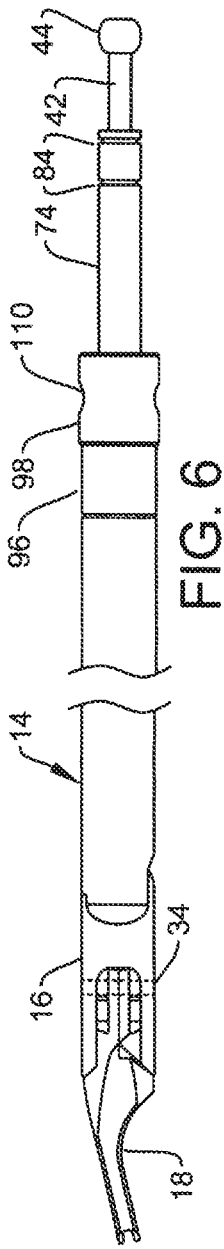

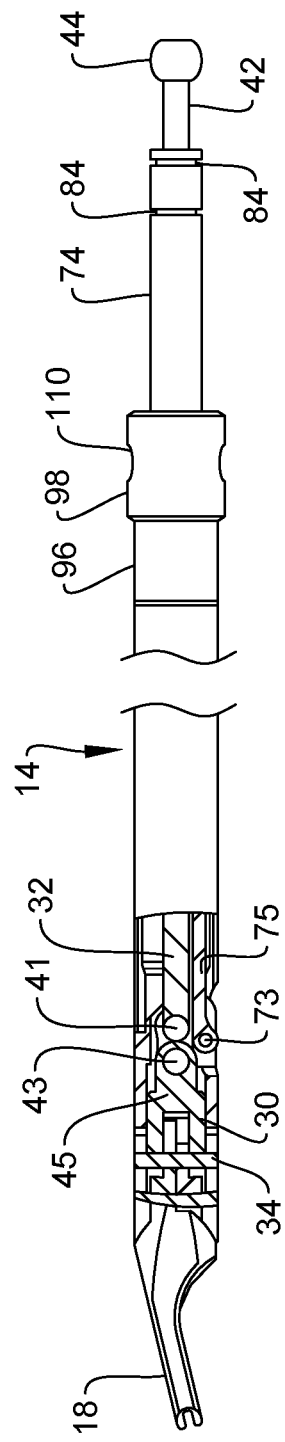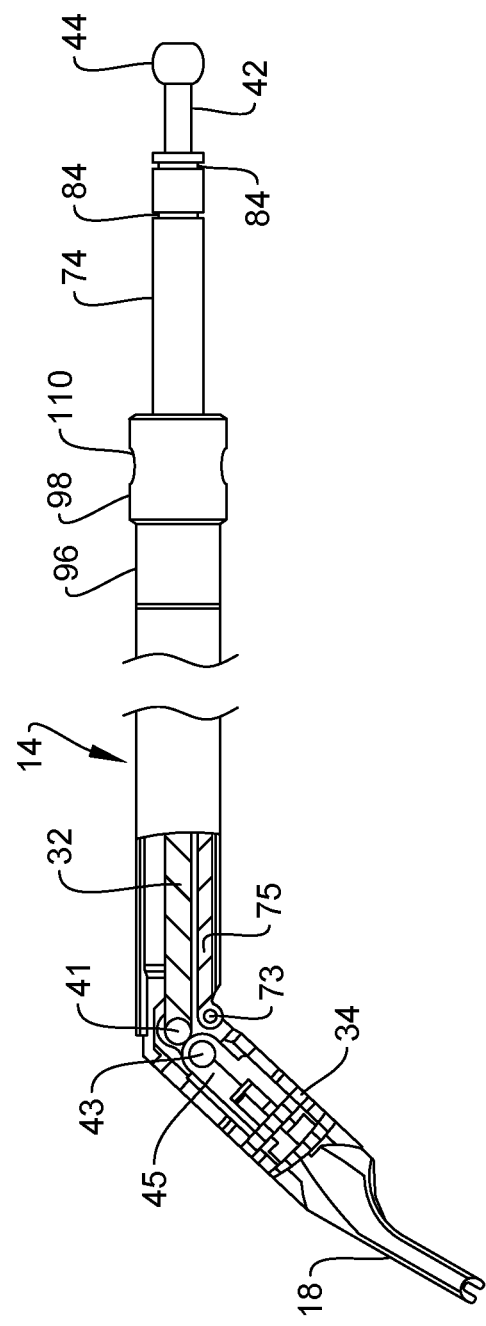

SURGICAL APPLIANCE

RELATED APPLICATIONS

This application claims the benefit of Provisional Application No. 62/581,729 filed Nov. 5, 2017, the entirety of which is incorporated herein in its entirety by reference.

BACKGROUND OF THE INVENTION

1. Field of the Invention

This invention relates generally to surgical appliances and more particularly to devices for applying ligation clips.

2. Antecedents of the Invention

During laparoscopic and endoscopic surgical procedures the surgeon must often terminate the flow of blood or other fluid through one or more vessels or ducts. Ligating clips have been applied to blood vessels or ducts to prevent the flow of body fluids through the vessel or duct. Endoscopic clip applying surgical appliances have been used for applying ligating clips, e.g., a polymeric ligating clip such as disclosed in US Patent Publication 2017-0311954 A1 (incorporated herein in its entirety by reference). Such ligating clips are typically fabricated from a biocompatible material and are usually compressed over a vessel or duct. Once applied to the vessel or duct, the compressed clip terminates the flow of fluid through the vessel or duct.

The clip applying surgical appliances generally included effector jaws at a distal end of a barrel and a handle section at a proximal end of the barrel. A safety mechanism for actuating the effector jaws was positioned adjacent the proximal end.

Endoscopic or laparoscopic procedures were often performed remotely from an incision. As a result, the application of ligating clips had to be accomplished through a reduced field of view or with reduced tactile feedback for the surgeon. It was therefore desirable to improve the operation of the surgical appliance by providing an instrument having enhanced maneuverability and which is capable of articulating in multiple directions without requiring the practitioner to employ two hands and which precluded inadvertent actuation of effector jaws.

SUMMARY OF THE INVENTION

An improved surgical appliance for procedures, such as applying polymeric ligating clips, is configured for enhanced maneuverability and single handed operation. The surgical appliance includes a barrel having effector jaws mounted to a carrier which is secured to the distal end of the barrel. A handle section is positioned at the proximal end of the barrel. The handle section includes a grip for opening and closing the effector jaws. The handle section also includes a knob for articulating the carrier, a knob for rotating the barrel and a safety mechanism for automatically preventing inadvertent actuation of the grip.

From the foregoing compendium, it will be appreciated that an aspect of the present invention is to provide an improved surgical appliance of the general character described which is not subject to the aforementioned disadvantages of the antecedents of the invention.

A feature of the present invention is to provide an improved surgical appliance of the general character described which facilitates the application of ligating clips.

A consideration of the present invention is to provide an improved surgical appliance of the general character described which enables a surgeon to ligate vascular walls without undue manipulation.

Another aspect of the present invention is to provide an improved surgical appliance of the general character described which is well suited for employment with conventional ligation clips.

A further feature of the present invention is to provide an improved surgical appliance of the general character described which is well suited for economical mass production fabrication.

An additional consideration of the present invention is to provide an improved surgical appliance of the general character described with enhanced maneuverability.

To provide an improved surgical appliance of the general character described which is capable of articulating in multiple directions without requiring the practitioner to employ two hands is another aspect of the present invention.

A consideration of the present invention is to provide an improved surgical appliance of the general character described having a handle section with a grip for actuating effector jaws and a safety mechanism for automatically locking the grip to preclude inadvertent actuation.

An additional feature of the present invention is to provide an improved surgical appliance of the general character described having a handle section with a grip for actuating effector jaws mounted to a carrier secured to the distal end of a barrel, a knob for articulating the carrier, a knob for rotating the barrel and a latch for locking the grip.

Other aspects, features and considerations of the present invention in part will be obvious and in part will be pointed out hereinafter.

With these ends in view, the invention finds embodiment in various combinations of elements, arrangements of parts and series of steps by which the above-mentioned aspects, features and considerations and certain other aspects, features and considerations are attained, or with reference to the accompanying drawings and the scope of which will be more particularly pointed out and indicated in the appended claims.

BRIEF DESCRIPTION OF THE DRAWINGS

In the accompanying drawings, wherein one of the various possible exemplary embodiments of the invention is shown:

FIG. 3 is a fragmentary sectional view through a portion of the surgical appliance showing the effector jaws in an open position;

FIG. 4 is a side elevation view thereof:

FIG. 5 is a fragmentary sectional view through a portion of the surgical appliance showing the effector jaws in a closed position;

FIG. 6 is a side elevation view with the jaws in a closed position:

FIG. 10 is a fragmentary sectional view through a portion of the surgical appliance, similar to FIG. 4 and showing the carrier coaxial with the barrel;

FIG. 11 is a fragmentary sectional view through a portion of the surgical appliance and showing the carrier in an articulated position;

DESCRIPTION OF THE INVENTION

Figure 1:
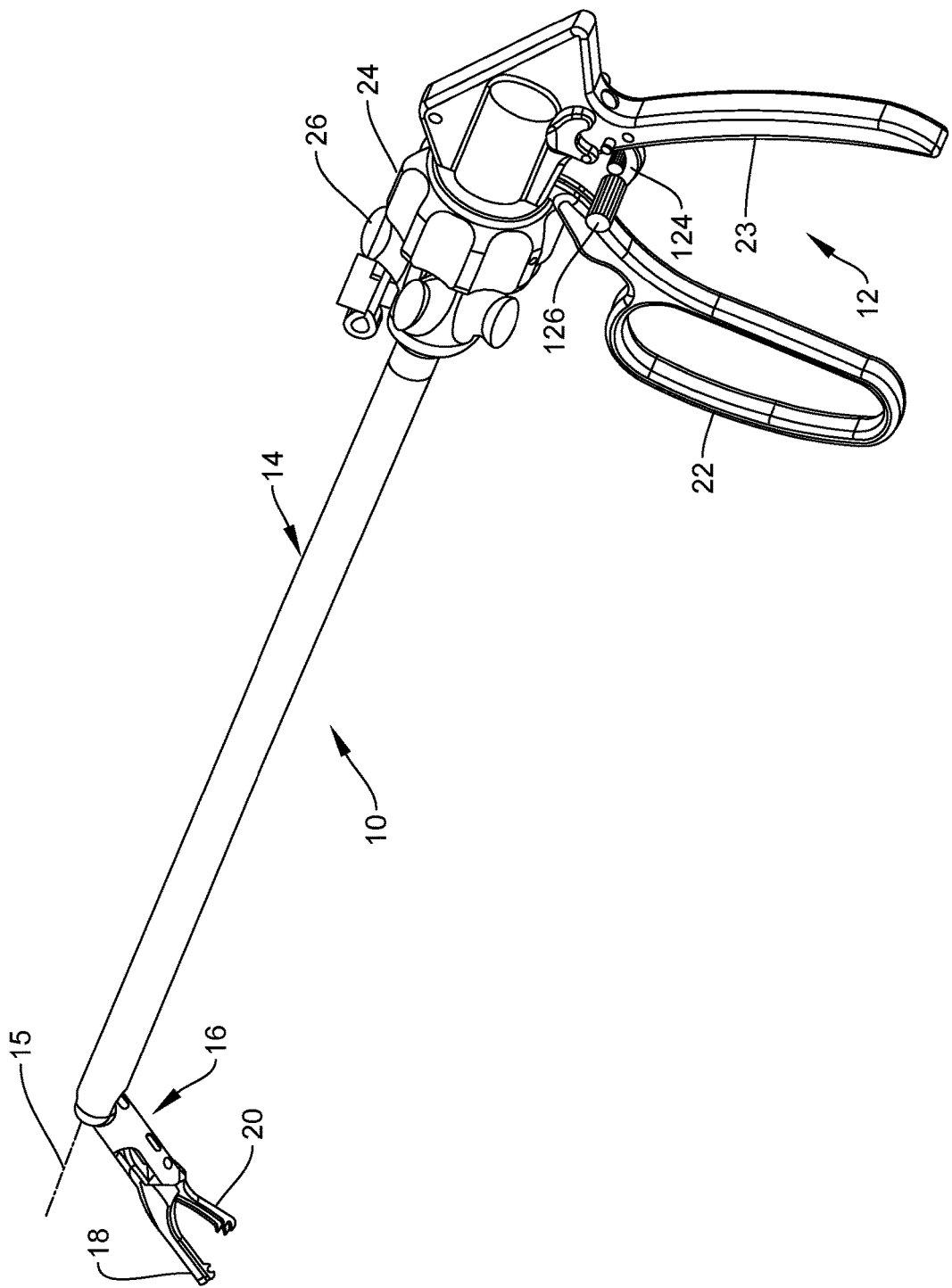
FIG. 1 is an isometric view of a surgical appliance constructed in accordance with and embodying the invention and showing a pair of effector jaws mounted to a carrier at the distal end of a barrel and a handle section at the proximal end of the barrel.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Applicants do not intend for any term in the specification or claims to be ascribed an uncommon or special meaning unless explicitly set forth as such. Further, the present invention encompasses present and future known equivalents to the known components referred to herein by way of illustration.

With reference now to the drawings wherein the reference numeral 10 denotes a surgical appliance constructed in accordance with and embodying the invention and which may be employed for procedures such as applying polymeric ligation clips. The appliance 10 includes a proximal handle section 12, a hollow cylindrical main barrel 14, which extends along a longitudinal axis 15 and a carrier 16, which carries a pair of effector jaws 18, 20. The handle section 12 includes a grip 22, a stock 23, an articulation knob 24 and a barrel rotation knob 26, all of which are positioned in proximate relationship to one another for single handed manipulation, e.g. squeezing and releasing the grip 22 by a practitioner's fingers with the practitioner's palm resting on the stock 23 as well as rotation of the knobs 24 and 26 by the practitioner's thumb and forefinger.

Figure 2:
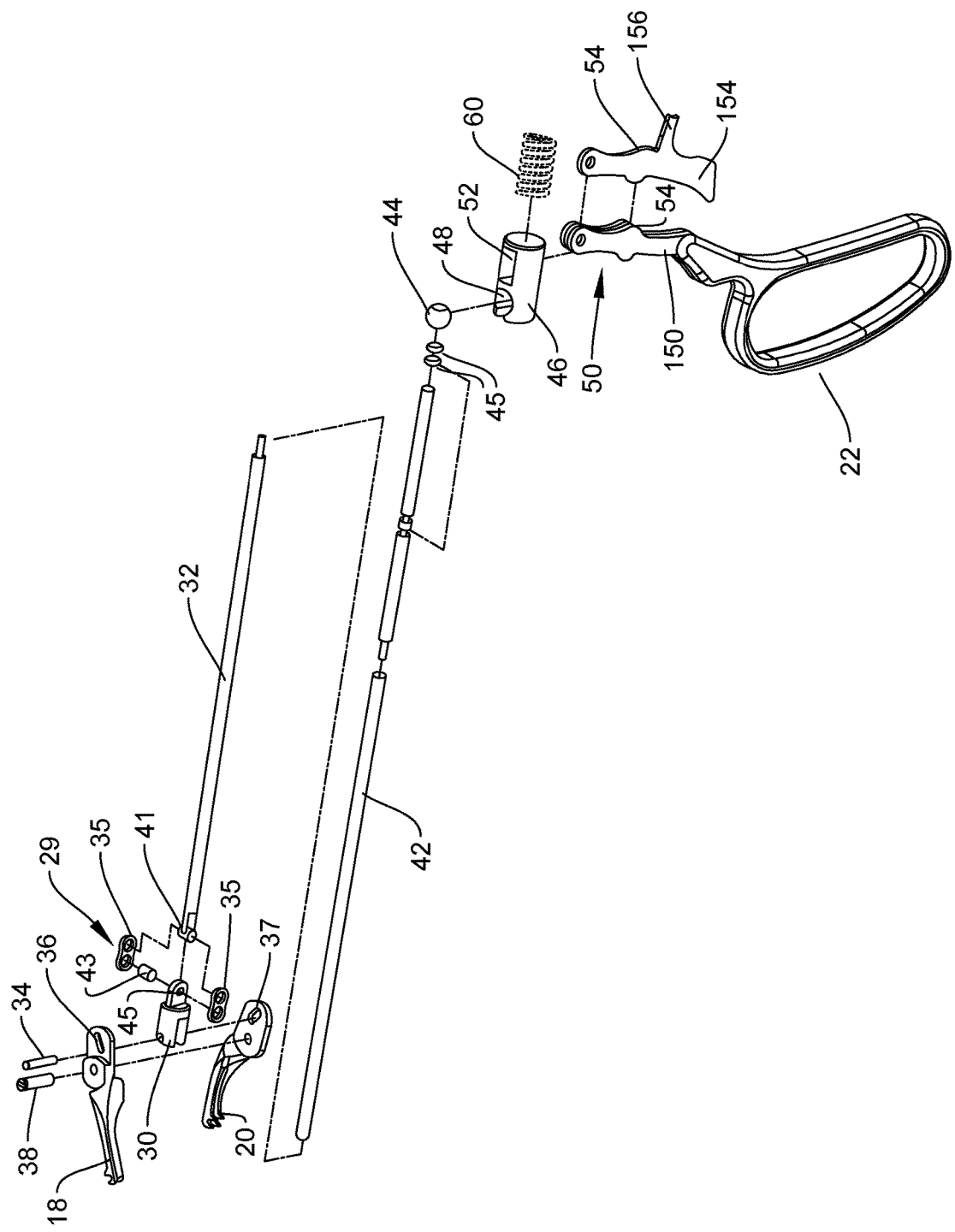
FIG. 2 is an exploded view of components for closing and opening the effector jaws.
Figure 9:
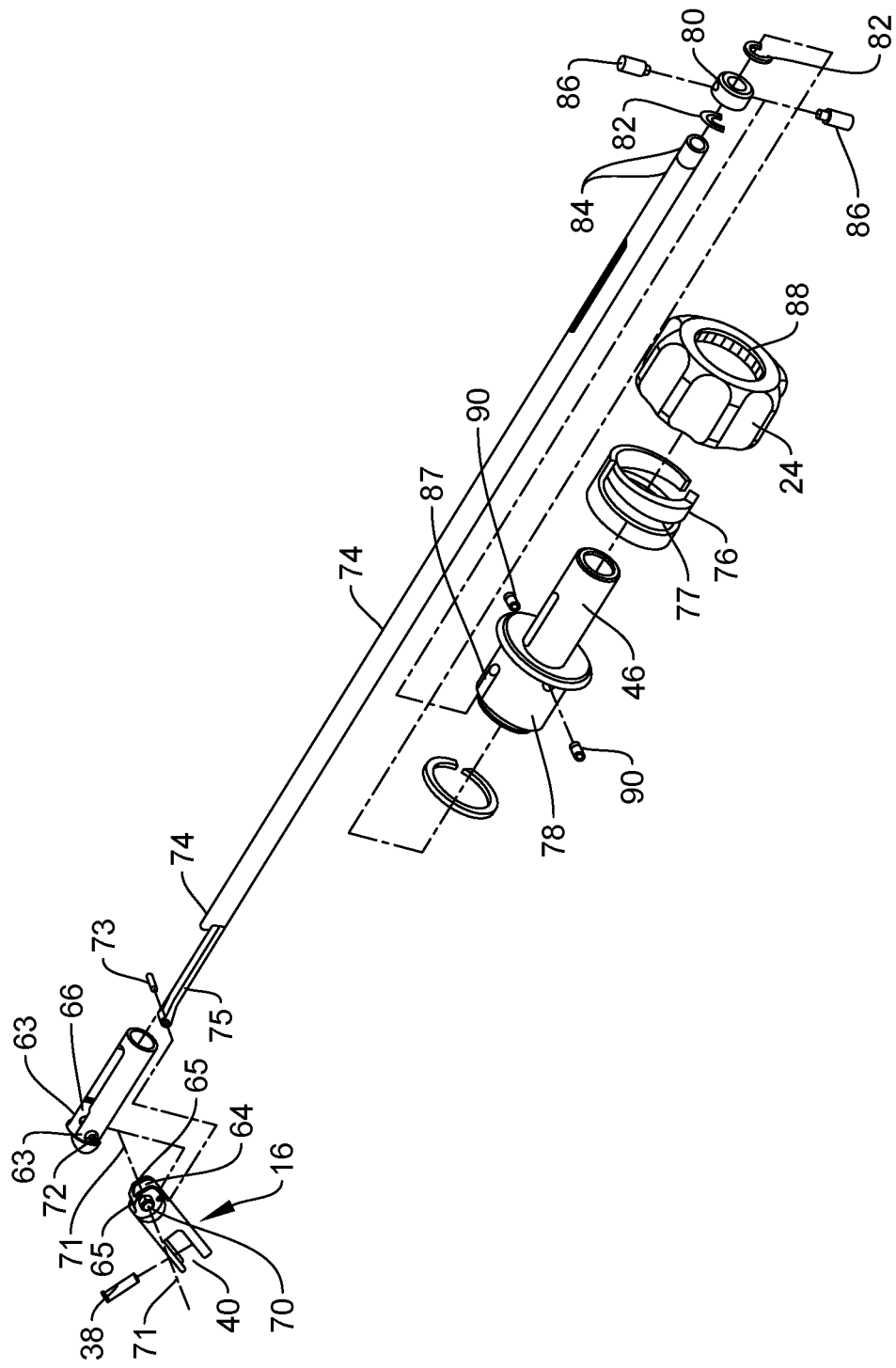
FIG. 9 is an exploded view of components for articulation of the carrier.

With reference to FIG. 2, it will be noted that the jaws 18, 20, are actuated through a terminal clevis 30 joined to the end of a rod 32 with a link 29, similar to a single link of a roller chain. A journal 41 projects from the distal end of the rod 32 through proximal apertures of a pair of side panels 35 and a pin 43 extends through distal apertures of the side panels and an aperture of a clevis flange 45. A further pin 34 extends through opposed faces of the clevis 30 and engages curved cam slots 36, 37 in the jaws 18, 20, respectively. Upon linear movement of the clevis 30 and rod 32, the jaws 18, 20 pivot about a pin 38 which extends through a yoke 40 of the carrier 16 as illustrated in FIG. 9. Portions of the jaws 18, 20 are received within the yoke 40.

Figure 7:
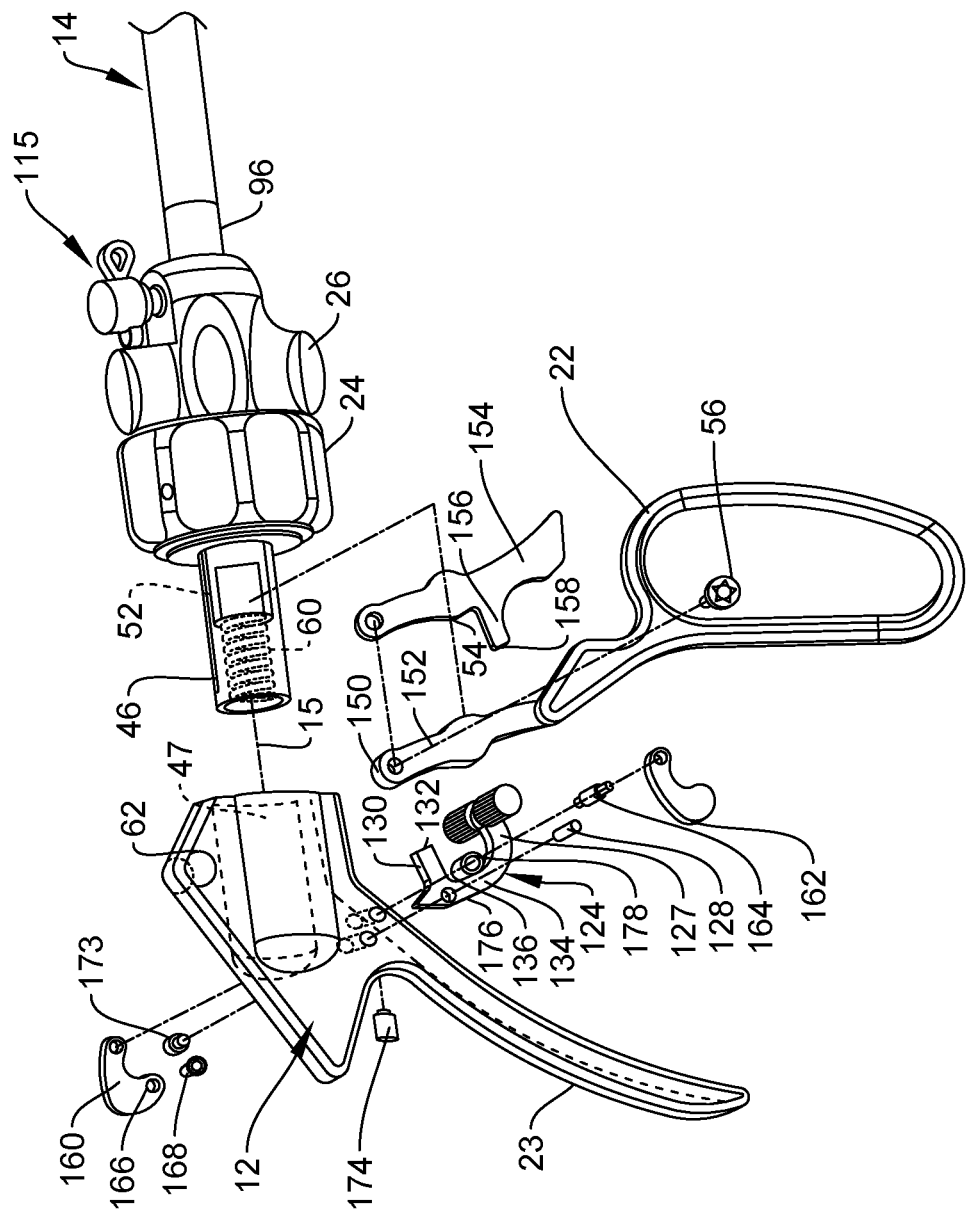
FIG. 7 is an exploded view of handle section components for closing and opening the effector jaws with a safety mechanism in an orientation for automatically precluding inadvertent actuation of the effector jaws.
Figure 8:
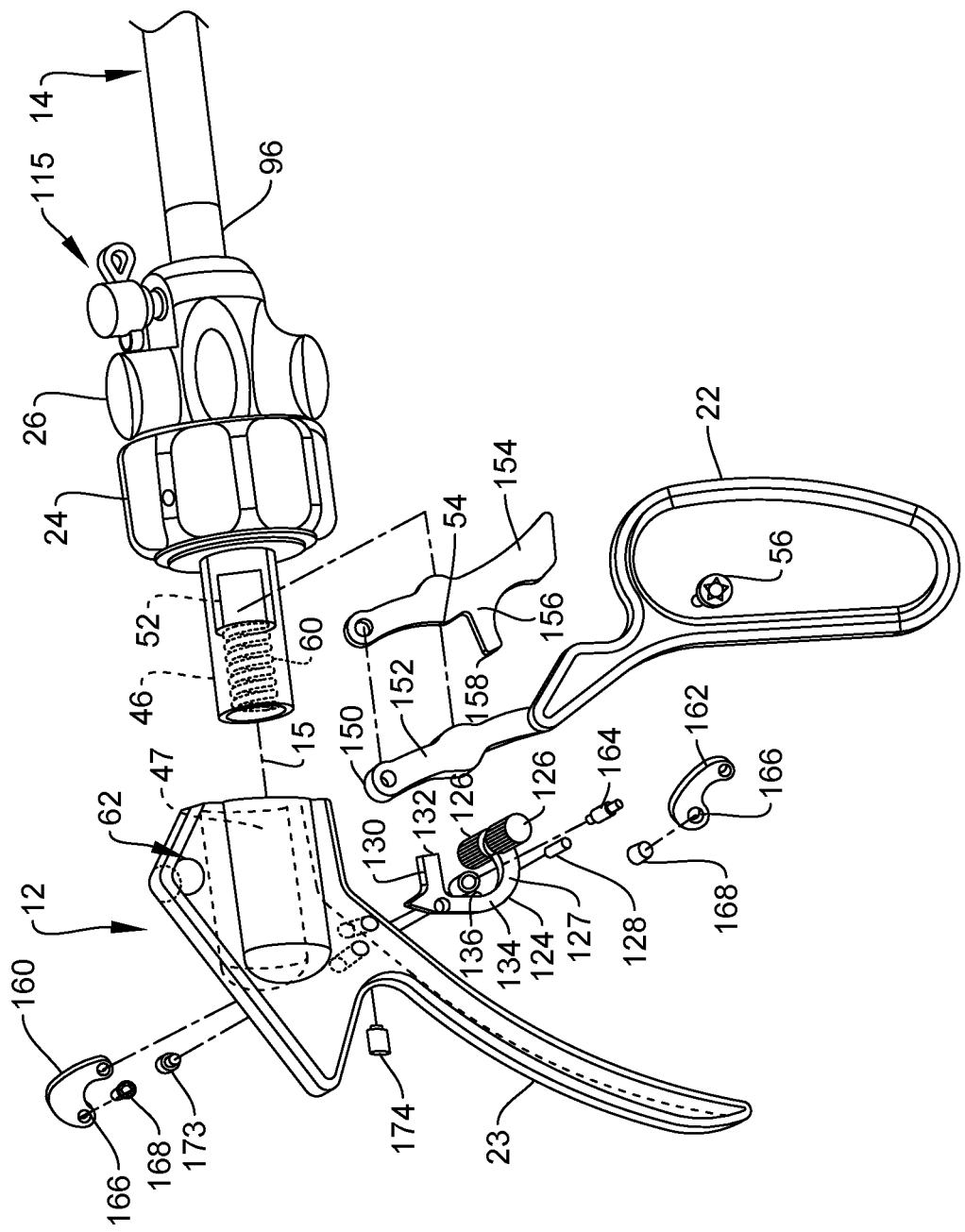
FIG. 8 is an exploded view of handle section components for closing and opening the effector jaws with the safety mechanism in an unlocked orientation permitting repeated actuation of the effector jaws.

A proximal end of the rod 32 is fixed to the distal end of a drawbar 42 which includes a ball 44 at its proximal end. A cylindrical linear actuator 46 is housed within a hollow casing 47 of the handle section 12 and includes a socket 48 wherein the ball 44 is received. A primary leg 50 of the grip 22 comprises a welded laminate of three panels 150, 152 and 154 and cam surfaces 54 which are received in a slot 52 of the linear actuator 46. With reference to FIG. 7, it will be noted that when the grip 22 is squeezed toward the stock 23, the primary leg 50 pivots about a pin 56 secured in an aperture 62 of the handle section 12, causing the linear actuator 46 and the ball 44 to move along the axis 15 in a proximal direction, compressing a return spring 60. Simultaneously, the drawbar 42, the rod 32 and the clevis 30 move toward the proximal end, causing the effector jaws 18, 20 to move from a normally open position, illustrated in FIG. 3, toward a closed position, illustrated in FIG. 5.

Referring now to FIG. 9, wherein components for articulation of the carrier 16 are illustrated, the carrier 16 includes a reduced thickness proximal channel flange 64 having spaced parallel panels 65 which are received between parallel spaced walls 63 of a channel 66 formed in a head sleeve 68. A journal 70 projects from each panel 65 and seat in apertures 72 of the channel walls 63. The head sleeve 68 is seated in the distal end of the barrel 14.

Articulation of the carrier 16 about an axis of rotation 71 concentric with the journals 70 is effected through reciprocal axial movement of a hollow tappet 74, which extends through the barrel 14. An end portion of a leg 75 which extends from a distal end of the tappet 74 is received between the panels 65. A pin 73 extends through an offset aperture 79 of the panels 65 and the end portion of the leg 75. Thus, axial movement of the tappet 74 effects articulation of the carrier 16 about the journals 70. Extending through the hollow tappet 74 is the drawbar 42 and a pair of gasket seals 45 is provided between the drawbar 42 and the tappet 74.

As illustrated in FIG. 9, rotation of the articulation knob 24 translates to axial movement of the tappet 74 through rotating a cylindrical cam 76 having a helix channel 77. The cam 76 is seated over a collar 78 which is fitted over the distal end of the linear actuator 46. The collar 78 is fitted over a ring 80 which is secured to the tappet 74 against relative axial movement by a pair of clips 82 which seat in corresponding grooves 84. A pair of diametrically opposed cam followers 86 is fixed to the ring 80 and engage the helix channel 77 of the cam 76.

The followers 86 also extend into a pair of diametrically opposed channels 87 of the collar 78. Thus, through engagement between the cam followers 86 and the cylindrical cam 76, rotation of the articulation knob 24 results in axial movement of the tappet 74 and pivotal movement of the carrier 16 about the axis of the pins 70.

Seated in the articulation knob 24 is an internal gear 88 which rotates with the knob 24. Upon rotation of the knob 24, the teeth of the gear 88 are engaged by a pair of ball detent latches 90 seated in diametrically opposed sockets of the collar 78 to increment rotation with yieldable and audible limit stops. It should be noted from FIG. 9 that the articulation knob 24, the cylindrical cam 76, the collar 78, the ring 80, the internal gear and the tappet 74 are coaxial.

For increased maneuverability within body cavities, the dimensions of the effector jaws 18, 20 and of the carrier 16 are ideally minimized. By way of example, the length of each effector jaw from its distal tip to the center of the pivot pin 38 would be in the order of 29 mm and with the carrier 16 articulated to a maximum offset angle of 50°, as illustrated in FIG. 10, the distance from the center of the carrier pivot pins 70 to the distal tip of the effector jaws 18, 20, in their open position, would be in the order of 50 mm.

Figure 12:
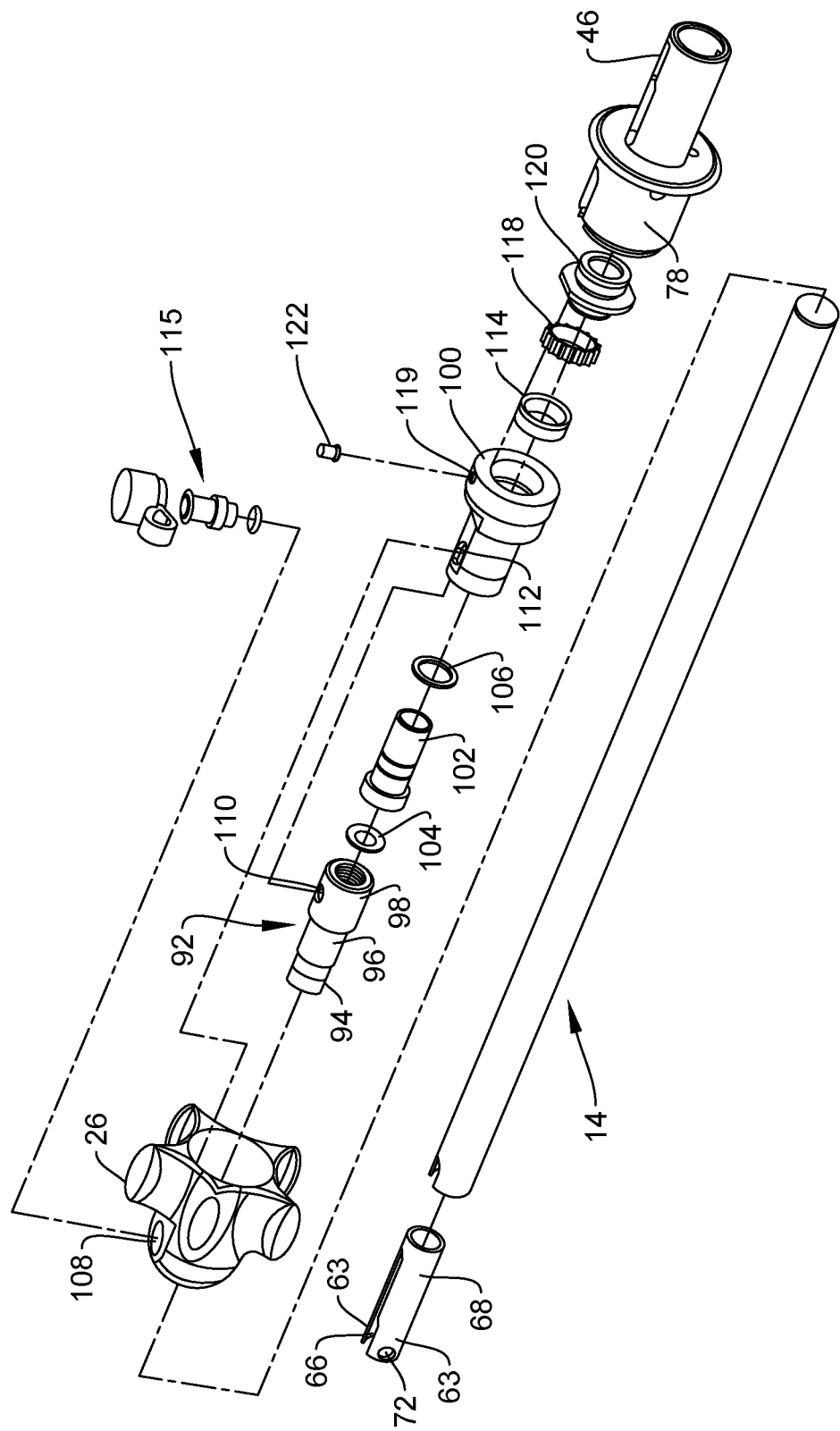
FIG. 12 is an exploded view of components for axial rotation of the barrel.

Referring now to FIG. 12, seated and fixed in the proximal end of the barrel 14 is a reduced diameter neck 94 of a stepped collar 92. A shoulder of an intermediate diameter portion 96 abuts the proximal end of the barrel 14. A larger diameter proximal portion 98 of the collar 92 is received in the bore of a main sleeve 100. Also positioned within the main sleeve bore is a transition sleeve 102, with a gasket 104 abutting the proximal end of the collar 92 and a further gasket 106 positioned over the sleeve 102. When assembled, a flushing passage is provided through registered openings 108, 110 and 112 in the barrel knob 26, the stepped collar 92 and the main sleeve 100 respectively. A flushing spigot assembly 115 is fitted into the barrel knob opening 108.

Seated in the proximal end of the main sleeve bore is a gasket 114, a ring gear 118 and terminal collar 120. It should be noted that the terminal collar 120 and the ring gear 118 remain stationery when the barrel rotation knob 26, the stepped collar 92 and the main sleeve 100 rotate in unison. Upon rotation of the main sleeve 100, the teeth of the ring gear 118 are engaged by a ball detent latch 122 seated in a socket 119 of the main sleeve 100 to increment rotation of the barrel 14 with yieldable and audible limit stops. From an examination of FIG. 12, it should be noted that the barrel 14, the barrel rotation knob 26, the stepped collar 92, the main sleeve 100, the transition sleeve 102, the ring gear 118, the terminal collar 120 and the collar 78 are coaxial.

Pursuant to the invention, a safety mechanism is provided to assure against unintentional actuation of the effector jaws 18, 20. With reference to FIG. 7 (wherein the grip 22 of the handle section 12 is shown in an automatic locking position), a lock/release lever 124 includes a pair of knurled finger bars 126 at a distal end of an integral arm 127. An upper portion of the lock/release lever 124 is seated within a hollow area of the stock 23. The lock/release lever 124 is configured to pivot about a pin 128 which extends through the stock 23.

Projecting distally from the upper portion of the lock/release lever 124 is an integral latch 130 having a concave abutment end 132. Unitarily joining the arm 127 and the latch 130 is a bight 134 having a distal face 136 and a proximal face 176. It should be noted that the panel 154 includes a proximally projecting strike leg 156 having an abutment end 158.

Figure 14:
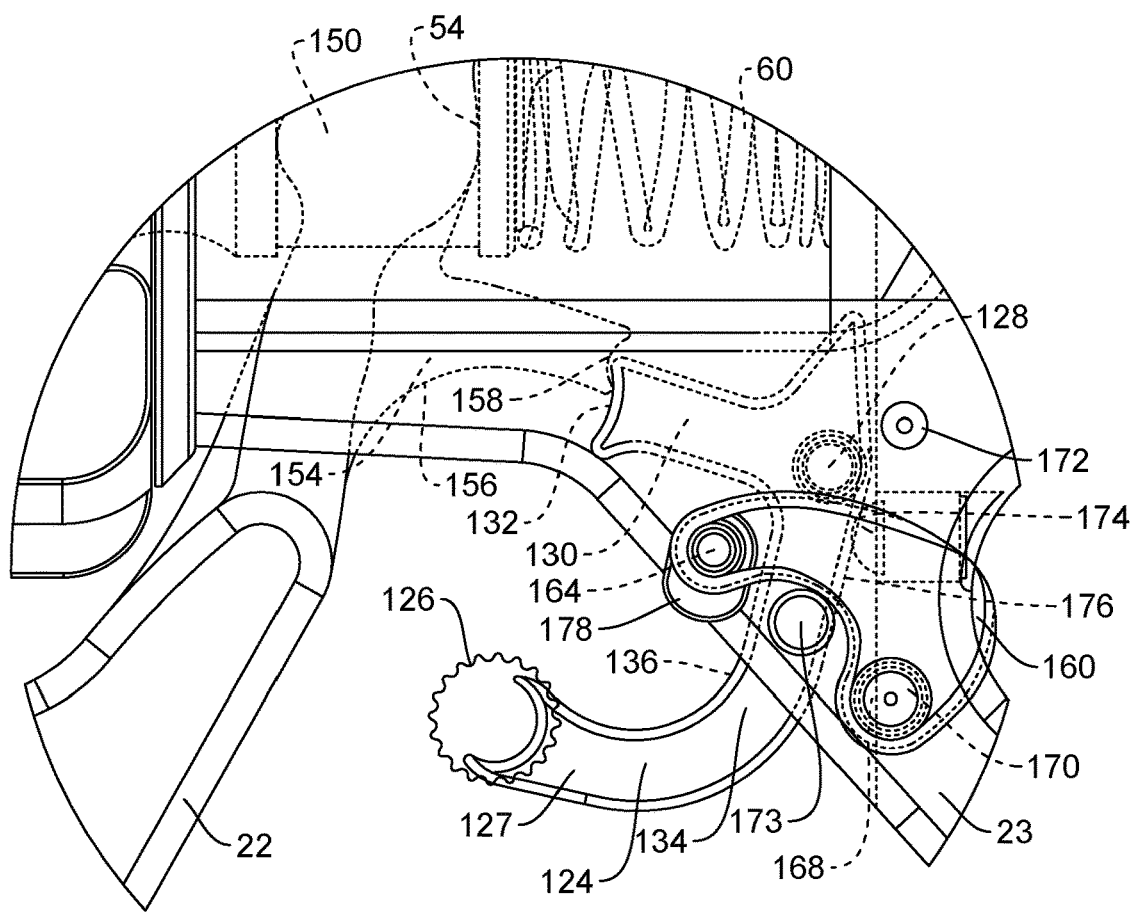
FIG. 14 is an enlarged view of a portion circled in FIG. 13.
Figure 16:
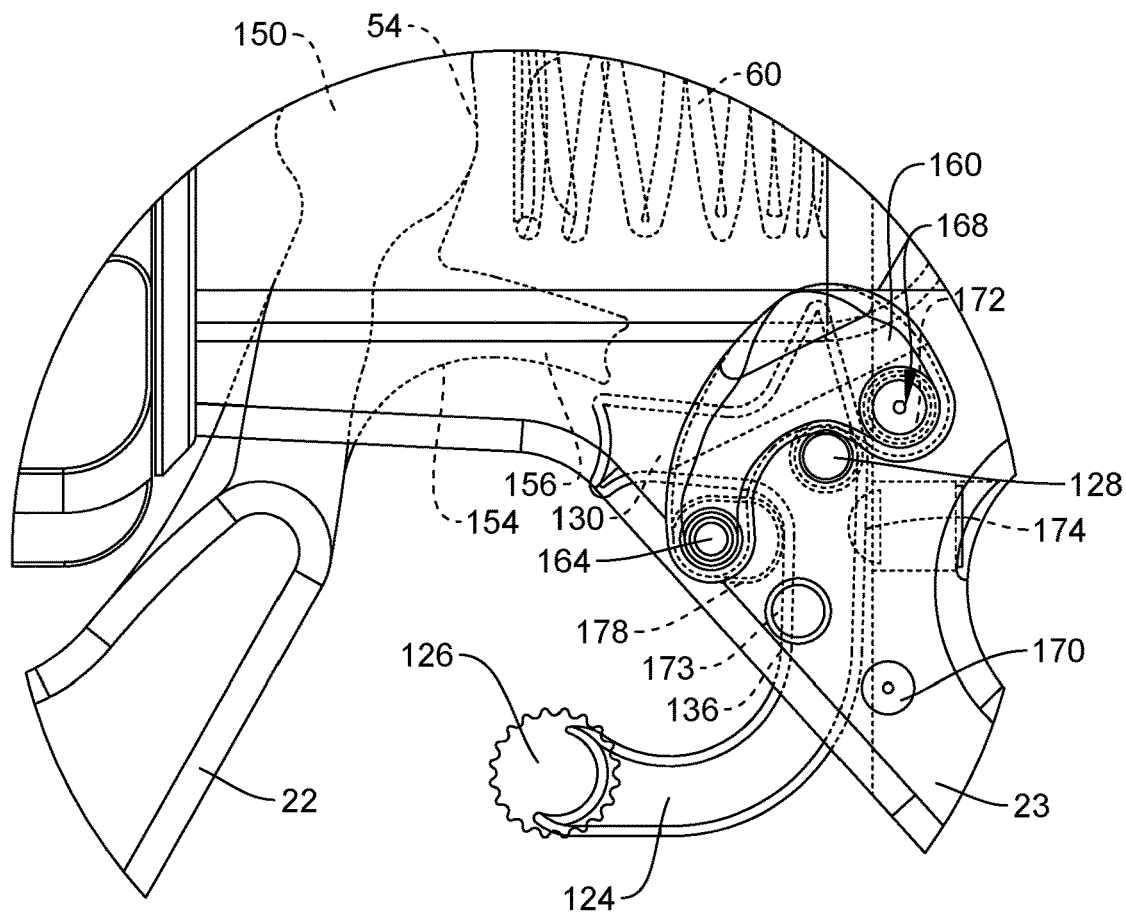
FIG. 16 is an enlarged view of a portion circled in FIG. 15.

A left side toggle arm 160 and a right side toggle arm 162 are fixed to opposite ends of a cam shaft 164 for rotation along opposite faces of the handle section 12 between an automatic lock position shown in FIG. 14 and an unlocked position, shown in FIG. 16. The inner face of each toggle arm includes a recess 166 which receives a ball latch 168. The ball latch 168 seats in a detent 170 in the locked position and in a detent 172 when the toggle arms are in the unlocked position. A stop pin 173 prevents further rotation of the toggle arms when the ball latch seats in the detent 170.

As best shown in FIG. 14, with the toggle arms 160, 162 in the automatic lock position, the grip 22 is prevented from movement in a proximal direction due to abutting contact between the respective abutment ends 132 and 158. A spring loaded ball assembly 174 is seated in the proximal end of the handle section 12 and bears against the proximal face 176 of the bight 134 while a cam 178, fixed to the cam shaft 164, abuts the distal face 136 of the bight 134.

A surgeon may unlock the grip 22 by grasping the knurled finger bars 126 and pulling the lock/release lever 124 proximally, against the bias of the spring loaded ball assembly 174, causing the lock/release lever 124 to rotate about the pin 128, whereby the strike leg 156 will no longer be aligned with the latch 130. The grip 22 may then be pulled proximally, causing the effector jaws 18, 20 to open for engaging or releasing a ligating clip, for example. Upon release of the knurled finger bars 126, the lock/release lever 124 returns to its FIG. 14 position, due to the bias of the spring ball assembly 174 against the proximal face 176.

Figure 13:
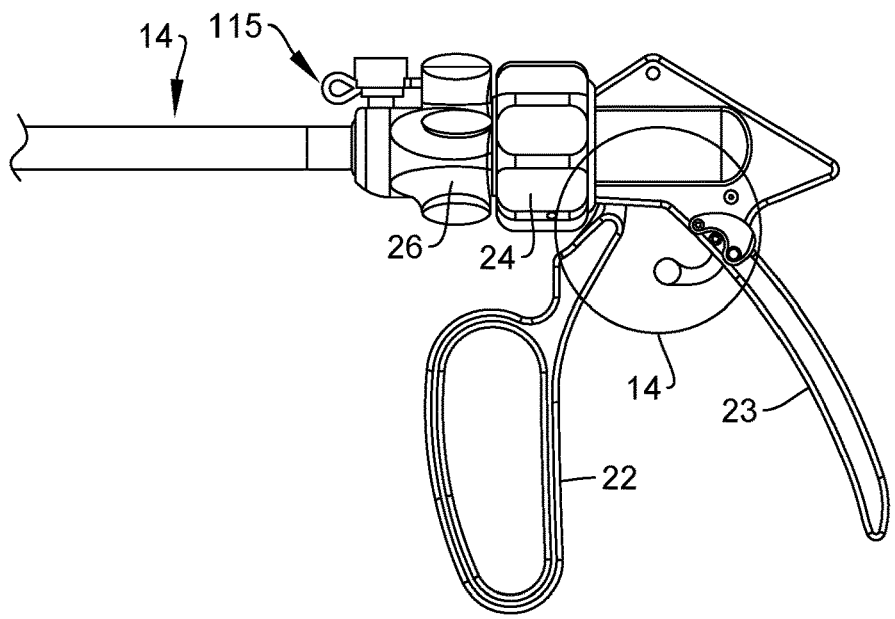
FIG. 13 is a fragmentary side elevation view of the surgical appliance, with the safety mechanism in an automatic locking position.
Figure 15:
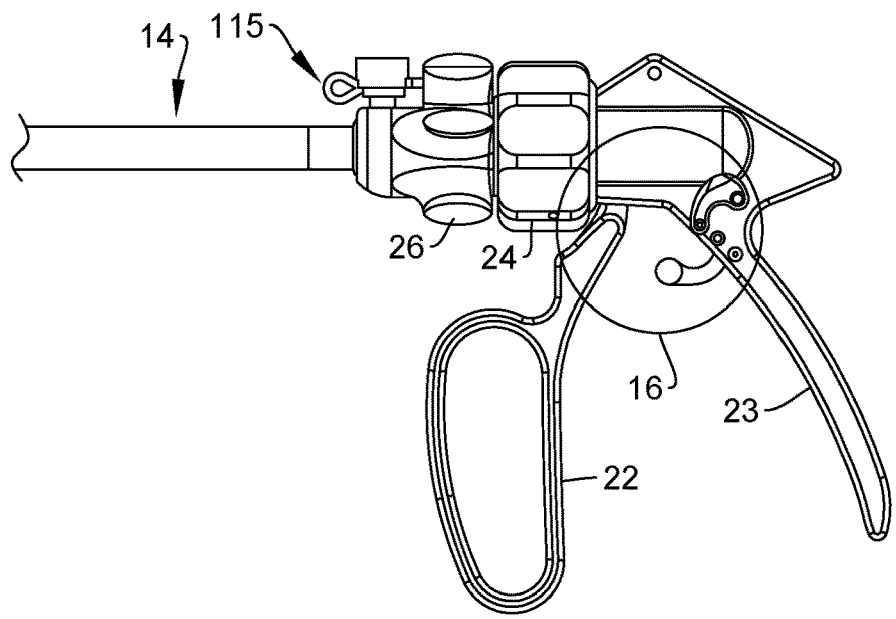
FIG. 15 is a fragmentary side elevation view of the surgical appliance, with the safety mechanism unlocked.

In FIG. 16, the safety mechanism components are shown disengaged, so that the grip 22 may be pulled without requiring the lock/release lever 124 to be rotated. To disengage the safety mechanism, the toggle arms 160, 162 are rotated with the cam shaft 164 approximately 90° counter-clockwise (as viewed from FIGS. 13-15) until the ball latch 168 seats in the detent 172, as shown in FIG. 16. Rotation of the cam shaft 164 causes the cam 178 to bear against the distal face 136 and rotates lock/release lever 124 in a counterclockwise direction, against the bias of the spring ball assembly 174 to its FIG. 16 position, wherein the strike leg 156 is no longer aligned with the latch 130 and the grip 22 may be freely actuated repeatedly throughout a surgical procedure.

In the figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only; the interchanging and substitution of these teachings with other teachings in this application are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

Having described the preferred embodiment of the invention, it will now become apparent to one of ordinary skill in the art that other embodiments incorporating the concept may be used. Moreover, those of ordinary skill in the art will appreciate that the embodiment of the invention described herein can be modified to accommodate and/or comply with changes and improvements in the applicable technology and standards referred to herein.

Variations, modifications, and other implementations of what is described herein can occur to those of ordinary skill in the art without departing from the spirit and the scope of the invention as claimed. It is felt therefore that these embodiments should not be limited to the disclosed embodiment but rather should be limited only by the spirit and scope of the appended claims.

Having thus described the invention, there is claimed as new and desired to be secured by Letters Patent:

1. A surgical appliance comprising an elongate barrel, a carrier secured in a distal end of the barrel, effector jaws mounted to the carrier, a rod or cable positioned within the barrel, a distal end of the rod or cable operatively connected to the effector jaws for opening and closing the effector jaws, a handle at the proximal end of the barrel, the handle including a linear actuator, a proximal end of the rod or cable being operatively connected to the linear actuator, the linear actuator having a slot, the handle further including a pivotally mounted grip, the grip including a primary leg, the primary leg being received in the slot, whereby pivotal movement of the grip results in linear movement of the rod or cable and movement of the effector jaws relative to one another, the handle further including a barrel rotation knob and a sleeve, the barrel rotation knob, the barrel and the sleeve being coupled to rotate in unison, a ring gear received in the sleeve, the ring gear being fixed against rotation, the handle further including a detent latch extending radially through the sleeve, the detent latch engaging the ring gear, whereby rotation of the barrel rotation knob is incremented with yieldable and audible limit stops.

2. The surgical appliance in accordance with claim 1 wherein the handle includes a carrier articulation knob and a safety mechanism for preventing the effector jaws from closing as a result of inadvertent operation of the grip.

3. The surgical appliance in accordance with claim 2 wherein the safety mechanism includes a lever rotatable from a lock position, wherein the grip is precluded from rotating, to an unlock position, wherein the grip is not precluded from rotating, the safety mechanism further including a spring element biasing the lever toward the lock position.

4. The surgical appliance in accordance with claim 1 wherein each effector jaw includes a cam slot and a pin which is operatively connected to the distal end of the rod or cable, the pin extending transversely through the cam slots, whereby linear movement of the rod or cable moves the effector jaws relative to one another.

5. The surgical appliance in accordance with claim 4 wherein the distal end of the rod or cable is joined to a terminal link and the pin extends through opposed faces of the terminal link.

6. The surgical appliance in accordance with claim 1 further including a return spring which bears against the linear actuator to urge, the linear actuator and the rod or cable in a distal direction such that the effector jaws are normally open.

7. The surgical appliance in accordance with claim 1 wherein the primary leg includes a laminate of panels having cam surfaces, the cam surfaces being received in the slot.

8. The surgical appliance in accordance with claim 1 wherein the barrel, the barrel rotation knob, the sleeve and the ring gear are coaxial.

9. A surgical appliance comprising an elongate barrel having effector jaws mounted to a carrier secured in a distal end of the barrel, a bifurcated cylindrical head sleeve at a distal end of the barrel and a handle at a proximal end of the barrel, a channel formed at the distal end of the head sleeve the channel comprising a pair of parallel walls, the carrier having a flange at its proximal end, the flange being received between the parallel walls, the carrier being pivotally joined to the head sleeve at an axis of rotation, an axially movable tappet carried within the barrel, the tappet including a tappet leg pivotally joined to the flange at a point offset from the axis of rotation, the handle including an articulation knob, a cylindrical cam and a ring having at least one cam follower projecting radially therefrom, the at least one cam follower being engaged in a channel of the cylindrical cam, the ring being seated over a proximal end of the tappet, the ring being secured against axial movement relative to the tappet, the articulation knob and the cylindrical cam rotating in unison, the cylindrical cam being positioned over the ring, whereby rotation of the articulation knob and engagement between channel and the at least one cam follower results in axial movement of the tappet and articulation of the carrier about the axis of rotation relative to the barrel.

10. The surgical appliance in accordance with claim 9 further including an internal gear seated in the articulation knob and rotating in unison therewith, the articulation knob being seated over a collar which is fixed against rotation, the collar including at least one ball detent latch registered with and engaging the internal gear whereby rotation of the rotation articulation knob is incremented with yieldable and audible limit stops.

11. The surgical appliance in accordance with claim 9 wherein the articulation knob, the cylindrical cam, the ring and the tappet are coaxial.

12. A surgical appliance comprising an elongate barrel, effector jaws positioned adjacent a distal end of the barrel, a rod or cable positioned within the barrel, a distal end of the rod or cable operatively connected to the effector jaws for opening and closing the effector jaws, the effector jaws transitioning from an open position to a closed position when the rod or cable is moved in a proximal direction, a handle at the proximal end of the barrel, the handle including a grip operatively connected to a proximal end of the rod or cable the grip being rotatable in a proximal direction to close the effector jaws and a safety mechanism for preventing the effector jaws from closing due to inadvertent operation of the grip, the safety mechanism including a lever rotatable from a lock position, wherein the grip is precluded from rotating in a proximal direction, to an unlock position, wherein the grip is not precluded from rotating in a proximal direction, the mechanism further including a spring element biasing the lever toward the lock position and a cam which is rotatable to bear against a surface of the lever to maintain the lever in the unlock position against the bias of the spring element; the surgical appliance further including a latch projecting distally from the lever, the grip including a strike leg which projects in a proximal direction, the latch being positioned to block the strike leg and preclude the grip from rotating in a proximal direction when the lever is in the lock position.

13. The surgical appliance in accordance with claim 12 wherein the lever includes a finger bar engageable to grasp and rotate the lever from the lock position to the unlock position wherein the grip may be actuated, the lever returning to the lock position under the bias of the spring element.

14. The surgical appliance in accordance with claim 13 wherein the cam is fixed to a shaft, an end of the shaft being fixed to a toggle arm, the toggle arm being rotated to rotate the cam to or from positions wherein the lever is placed in the unlocked position without engaging the finger bar.

15. The surgical appliance in accordance with claim 14 including a further toggle arm fixed to the opposite end of the shaft, each toggle arm including a ball latch mechanism which seats at one detent corresponding to the lever unlock position and another detent corresponding to the lever lock position.

16. The surgical appliance in accordance with claim 12 wherein the grip includes a laminate of panels, the strike leg projecting from at least one of the panels.

17. The surgical appliance in accordance with claim 12 wherein the lever includes a distally projecting arm, the finger bar being positioned at the end of the arm and projecting laterally therefrom, the lever further including a bight spanning between the arm and the latch.

18. The surgical appliance in accordance with claim 17 wherein the bight includes a proximal face and a distal face, the spring element engaging the proximal face and the cam engaging the distal face.

19. A surgical appliance comprising an elongate barrel having effector jaws mounted to a carrier secured in a distal end of the barrel, the carrier having an axis of rotation relative to the barrel, a linearly movable tappet carried within the barrel, the tappet being pivotally joined to the carrier at a point offset from the axis of rotation, the handle including an articulation knob, a cylindrical cam element and a cam follower element, the cam follower element being engaged in a channel of the cylindrical cam element, rotation of one element resulting in linear movement of the other element, the other element being operatively connected to the tappet, the articulation knob being operably connected to the cylindrical cam element and the cam follower element and being secured against axial movement relative to the tappet, whereby rotation of the articulation knob and engagement between the channel of the cylindrical cam element and the cam follower element results in axial movement of the tappet and articulation of the carrier about the axis of rotation relative to the barrel.

* * * * *